(12) United States Patent
Imani et al.

(10) Patent No.: US 7,046,499 B1
(45) Date of Patent: May 16, 2006

(54) INTERNALLY GROUNDED FILTERING FEEDTHROUGH

(75) Inventors: Reza Imani, Moorpark, CA (US); Rodney J. Hawkins, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/958,968

(22) Filed: Oct. 4, 2004

(51) Int. Cl.
*H01G 4/35* (2006.01)

(52) U.S. Cl. ............ 361/302; 361/306.1; 174/152 GM; 607/5

(58) Field of Classification Search ............... 361/302, 361/306.1, 306.3, 301.3; 174/152 GM; 333/182–186; 29/25.42; 607/5, 36, 37
See application file for complete search history.

(56) References Cited

U.S. PATENT DOCUMENTS

| | | | |
|---|---|---|---|
| 5,817,130 A | 10/1998 | Cox et al. | 607/5 |
| 5,905,627 A | 5/1999 | Brendel et al. | 361/302 |
| 6,275,369 B1 * | 8/2001 | Stevenson et al. | 361/302 |
| 6,529,103 B1 | 3/2003 | Brendel et al. | 333/182 |
| 6,586,675 B1 | 7/2003 | Bealka et al. | 174/50.56 |
| 6,768,629 B1 * | 7/2004 | Allen et al. | 361/302 |

* cited by examiner

*Primary Examiner*—Anthony Dinkins

(57) ABSTRACT

A feedthrough device includes a conductive ferrule having an outer peripheral surface defining the outermost boundary of the feedthrough device, an insulator, a lead wire electrically isolated from the ferrule extending through the insulator, a filter capacitor adjacent the insulator through which the lead wire extends in conductive relation therewith, and a ground wire coupled to the ferrule and to the insulator within the outermost boundary of the feedthrough device. The ferrule has an inner peripheral surface defining an opening therethrough and each of the insulator and the filter capacitor has an outer peripheral surface proximate the inner peripheral surface, a counterbore in the outer peripheral surface of each of the insulator and filter capacitor, an end of the ground wire being received in the counterbore and brazed to the ferrule and insulator. Alternatively, an end of the ground wire is welded to the inner peripheral surface of the ferrule.

26 Claims, 10 Drawing Sheets

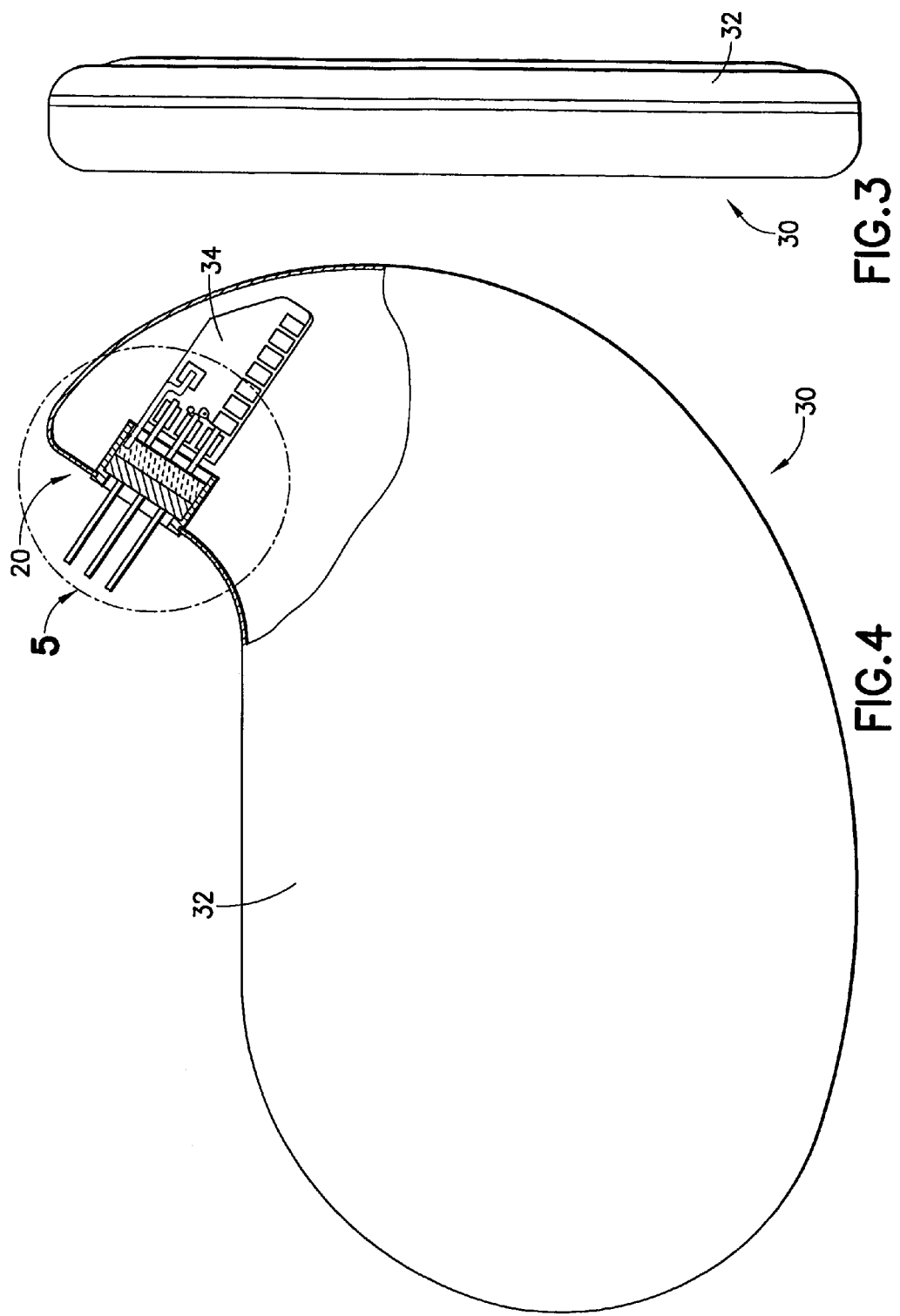

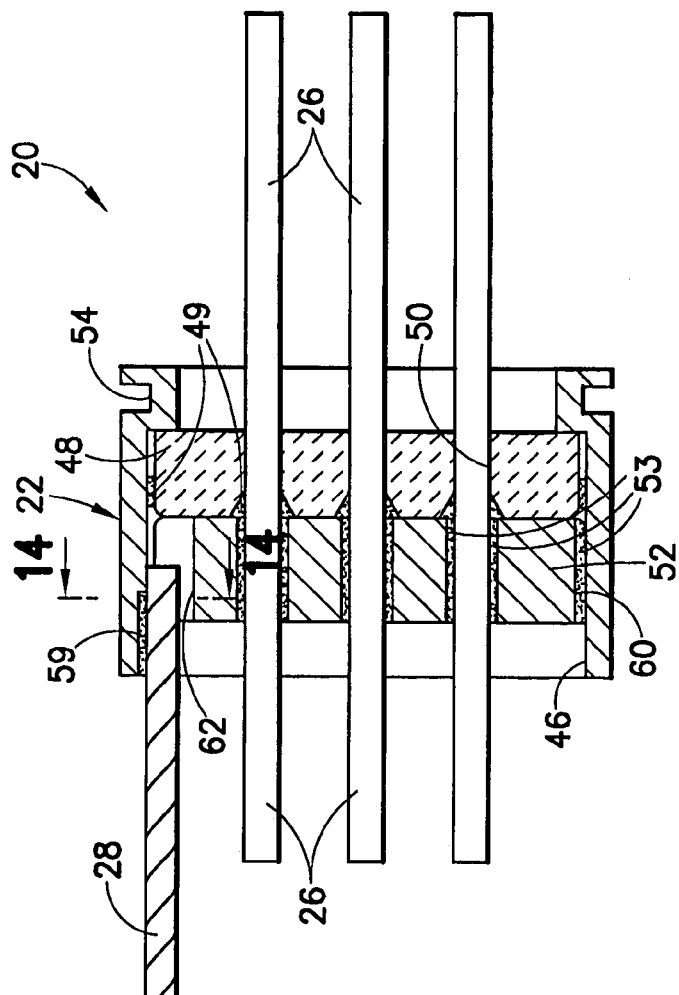
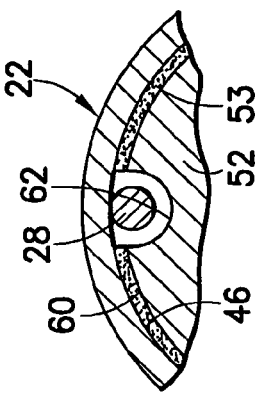
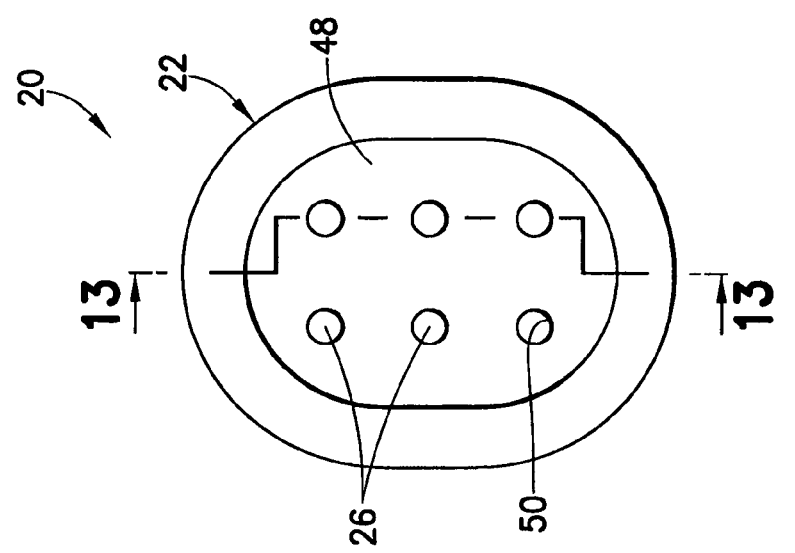
FIG.13
FIG.14
FIG.12

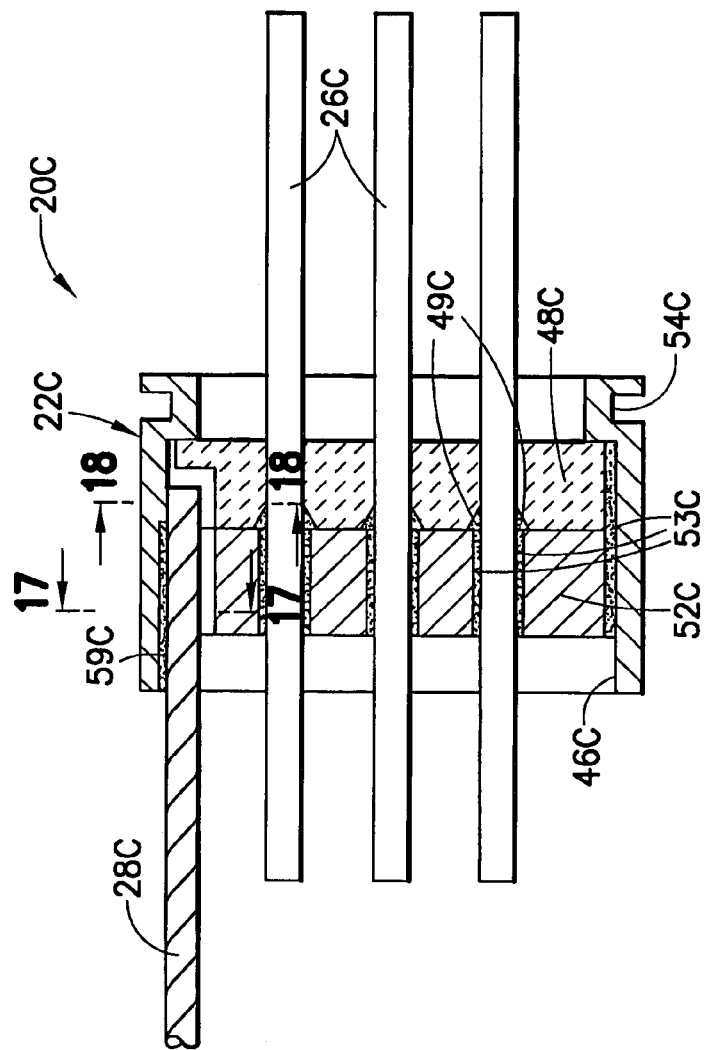
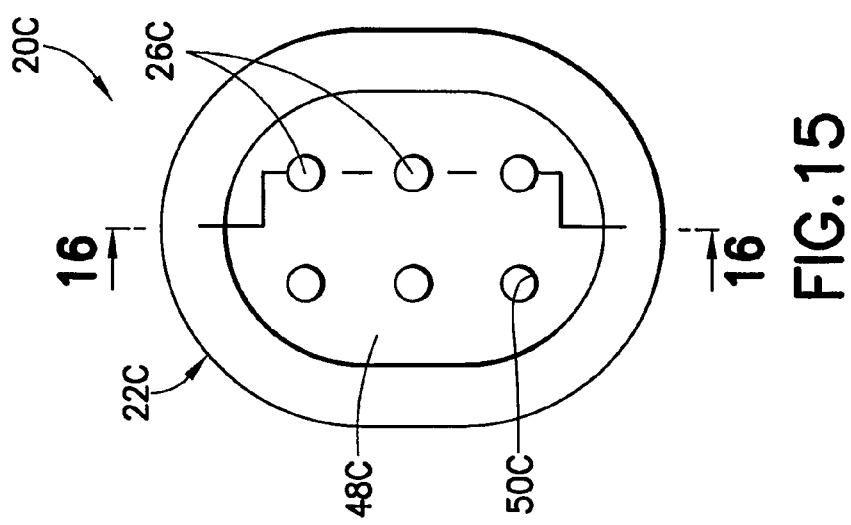

INTERNALLY GROUNDED FILTERING FEEDTHROUGH

FIELD OF THE INVENTION

The present invention is directed to feedthrough devices having grounded leads. In particular, the invention relates to feedthrough devices with internally grounded filtering leads that are suitable for use in implantable medical devices or pulse generators, such as pacemakers, defibrillators, and the like.

BACKGROUND OF THE INVENTION

A conventional implantable pacemaker or cardioverter/defibrillator system comprises at least one electrode attached to the heart and connected by a flexible lead to a shock or pulse generator. This generator is a combination of a power source and the microelectronics required for the system to perform its intended function. Many pacemakers and cardioverter/defibrillators in current use incorporate circuits and antennae to communicate non-invasively with external instruments called programmers. These implantable devices have the capability of correcting dangerous arrhythmias and fibrillation by applying selected stimulation patterns or high energy shocks. High energy shocks are used primarily to correct life-threatening fibrillations by essentially stopping the heart and allowing an appropriate rhythm to re-establish itself.

Implantable medical devices such as pacemakers, defibrillators, and other implantable pulse generators generally comprise one or more electrical leads in electrical communication with the pulse generator which emanate from the housing and typically terminate at a distal location within the patient. The leads transmit electrical signals to and from the device and, as such, are fabricated having a conductor made from a metal alloy to enable good conductivity. Because of their conductive properties, these leads effectively act as an antenna and thus tend to conduct unwanted electromagnetic interference (EMI) signals. These EMI signals may be transmitted to the medical device and interfere with normal operations. Sources of EMI signals are prevalent and include, for example, radio and TV transmitters, cellular telephones, medical electrosurgical equipment, microwave devices, welding equipment, security and surveillance systems, and other sources of radio frequency interference (RFI). In implantable cardioverter/defibrillators, charging and delivery of a defibrillating shock can cause EMI which adversely affects the sensing circuits or the operation of the device.

Two basic approaches may be employed to reduce the effects of unwanted EMI on implantable medical device operations. In the first approach, the medical device is enclosed in a metallic housing or shield which may be conductively connected to a ground reference of the device. In the second approach, a filtering circuit attenuates potential EMI before it reaches the circuitry of the medical device. The two approaches may be used separately or in a combined manner.

In most instances, the size of the feed-through must be minimized due to constraints on the size of the completed device. This is particularly applicable, but not limited to the situations encountered in implantable devices such as cardiac pacemakers, cardiac defibrillators, cochlear implants, implantable hearing devices, and the like. Feed-through devices and the leads attached thereto must be robust enough to withstand manufacturing processes and the usage of the devices, and at the same time be made economically. The size of the feedthrough device limits how small an implantable device can be, because the width of a pacemaker or defibrillator case must be, at minimum, slightly larger than the width of the feedthrough.

Conventional feedthrough devices typically include a metallic ferrule, an insulating material, and at least one wire lead. If the feedthrough is used in a medical implant, the materials used should be biocompatible and resistant to corrosion, because the feedthrough becomes part of a case that protects the electronics inside the body.

More particularly, feedthrough devices have been employed in implantable devices, as disclosed and described in U.S. Pat. No. 6,586,675 to Bealka et al., U.S. Pat. Nos. 6,529,103 and 5,905,627 to Brendel et al., and U.S. Pat. No. 5,817,130 to Cox et al., as examples. Typically, feedthrough devices include a metallic ferrule, which may have one or more flanges formed therein to facilitate mounting the device to the implantable medical device. The ferrule also has one or more openings through which a lead wire (or wires) may extend. Each lead wire is encapsulated and hermetically sealed within an insulating material that fills the remainder of the opening in the ferrule. The insulating material is bonded to both the lead wire and ferrule by glass sealing or brazing. The coupling of the above components must be done in such a way as to maintain a hermetic seal between each lead wire and the insulating material, and between the insulating material and the ferrule. Of the noted patents, only Bealka et al. discloses a ground wire which is mounted within the outer boundary of the ferrule, but the feedthrough device of that disclosure does not provide for signal filtration.

Some of the current practices employed for grounding electronic devices to a case in these feedthrough assemblies involve steps that use unnecessary space, are inefficient, and may cause yield problems. For example, one current practice includes attaching a lead directly to the case of the device, either by brazing or welding. However, in many instances, it is desirable for a lead to be grounded to the feedthrough upon delivery to an upper level assembly manufacturer. By having the ground wire in place prior to being delivered to an upper level assembly manufacturer, the upper level manufacturer is able to test the feedthrough device and any potentially attached electronics, rather than jeopardize the entire upper level assembly or case to which the device would be attached.

Current practice also involves welding a ground wire directly to a ferrule, away from the insulating material. Welding, however, is more labor intensive and expensive than brazing. A brazed joint is typically sturdier than a welded joint as well. Additionally, either brazing or welding the ground wire directly to the ferrule takes up a significant amount of space on the ferrule, because such a procedure requires an additional braze or weld joint. It also makes orienting the lead more difficult, because there is nothing supporting the sides of the ground wire. This additional braze joint must also be spatially separated from the original braze joints (those associated with the insulating material to metallic ferrule joints securing the wire lead) because the ground wire/ferrule braze joint can exert stress on the original braze joints, thus weakening both joints.

Additionally, brazing a ground wire into a separate opening on the ferrule also requires a separate braze load to be placed at the ground wire/ferrule interface. See, for example, the earlier mentioned Brendel et al. patent. Passing a ground wire through the ferrule in the manner of the patent, thus requiring an additional braze joint to be made, may adversely affect yields. As stated, a high integrity hermetic seal for medical implant devices is critical in order to prevent body fluids from penetrating the implanted device. Additionally, if the ground wire is to be placed in a thin area of the ferrule due to space constraints, assembly is more difficult because of the fixtures that would be required to hold the lead in position.

Furthermore, welding a ground wire to the ferrule after assembly of the feedthrough is also labor intensive and not as reliable. Welding a ground wire to the ferrule followed by brazing is more reliable but still labor intensive. This again requires a significant amount of space on the ferrule due to the additional braze joint that is necessary. In addition, this arrangement will not allow the ground wire to pass through the ferrule, which may be necessary for some implant devices.

In the special case in which a grounded lead must pass through the insulating material, present technology includes welding the ground wire to the ferrule or medical device case after assembly. For example, in the instance where a ground wire must pass through insulating material to ease attachment of a capacitor, it may be preferable to test the feedthrough/capacitor prior to welding the feedthrough assembly into the case that protects the electronics inside the body, as described above. This testing is impractical when the ground wire is welded to the case. If the ground wire is welded separately to the ferrule, the device requires more space.

There is also an industry practice of grounding a lead that is brazed to a ceramic. This involves laying a metallization layer or conductive member between the ferrule and the ground wire, across the surface of the ceramic, prior to brazing. The use of this procedure can cause yield problems due to braze flow between the ferrule and the ground wire, as capillary action may cause braze material to wick between the distinct braze joints, causing one or the other joint to have too much or too little braze.

Accordingly, there is a need in the art for a feedthrough device having a ground wire electrically coupled to the ferrule and located within the opening of the ferrule and the insulating material, providing efficient assembly and minimizing the overall size of the feedthrough device.

It was in light of the foregoing that the present invention was conceived and has now been reduced to practice.

SUMMARY

Feedthrough apparatus for an implantable medical device having a casing includes a conductive housing having an outer side, an inner side, and a peripheral surface with a continuous assembly groove therein for mounting on the casing of the implantable medical device. The conductive housing has first and second through bores extending between the outer side and the inner side in spaced apart, generally parallel, relationship. First and second filtered feedthrough assemblies are received, respectively, in the first and second through bores. Each filtered feedthrough assembly includes an insulative terminal, a filter capacitor, and a plurality of lead wires electrically isolated from the conductive housing supported on and extending through the insulative terminal and through the filter capacitor in conductive relation therewith. Also, a backfill port is provided on the conductive housing and has a passageway extending between the inner side and the outer side.

In one configuration, the invention includes two ceramic terminals with each having four leads embodied in one titanium housing. The terminals are gold brazed in the housing as are with the current quad feedthroughs. EMI filter capacitors are attached to the terminals and housing in a manner unchanged from the current manufacturing process.

In addition, the back fill port is designed as a feature of the housing. This manner of construction will save additional assembly steps for that component. This feature is dimensionally configured to simulate the currently used back fill port and to minimize the functional impact to the current manufacturing process.

The integration of the back fill port to the housing is required for the purpose of the invention but the invention is not limited to an eight pole feedthrough construction. Rather, this concept can easily be integrated into any other high voltage feedthrough design to achieve similar manufacturing benefits.

The design of the Integrated eight pole feedthrough is based on achieving manufacturability improvements of the feedthrough components, reducing thermal inputs to the feedthrough/output flex solder joints, enhancing weld requirements of feedthrough to case attachment and reducing assembly processes. Once this feedthrough design is implemented, it will eliminate all manufacturing processes associated with locating and welding of the back fill port.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is an end elevation view of a cardiac stimulation device with which the feedthrough device of the invention may be used;

FIG. 4 is a side elevation view of the cardiac stimulation device illustrated in FIG. 3;

FIG. 12 is an end elevation view of the feedthrough device of the invention illustrated in FIG. 1;

FIG. 13 is a cross section view taken generally along line 13—13 in FIG. 12;

FIG. 14 is a detail cross section view taken generally along line 14—14 in FIG. 13;

FIG. 15 is an end elevation view of another feedthrough device of the invention;

FIG. 16 is a cross section view taken generally along line 16—16 in FIG. 15;

DETAILED DESCRIPTION OF THE PREFERRED EMBODIMENTS

Figure 1:
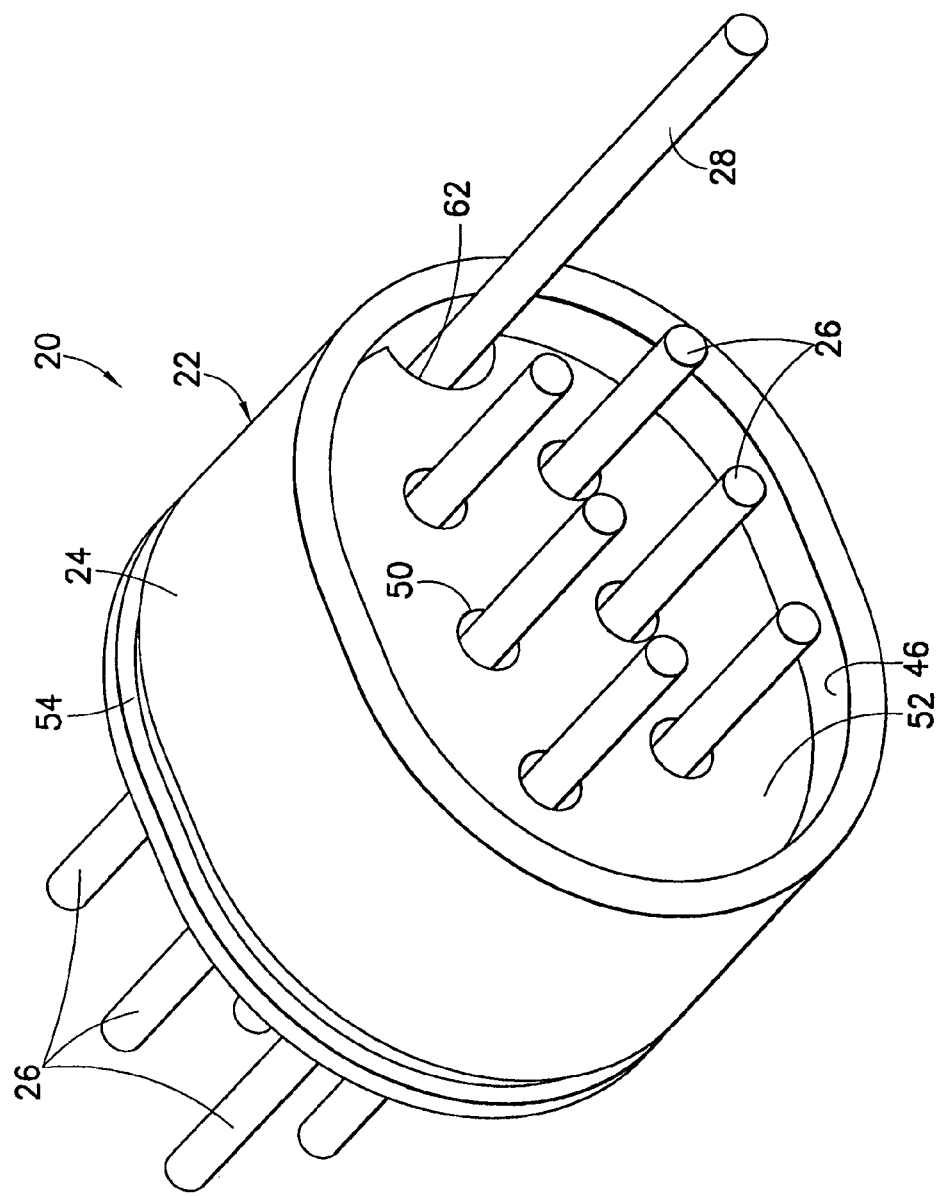
FIG. 1 is a perspective view illustrating a feedthrough device embodying the present invention as viewed from the housing of a medical implant device.
Figure 2:
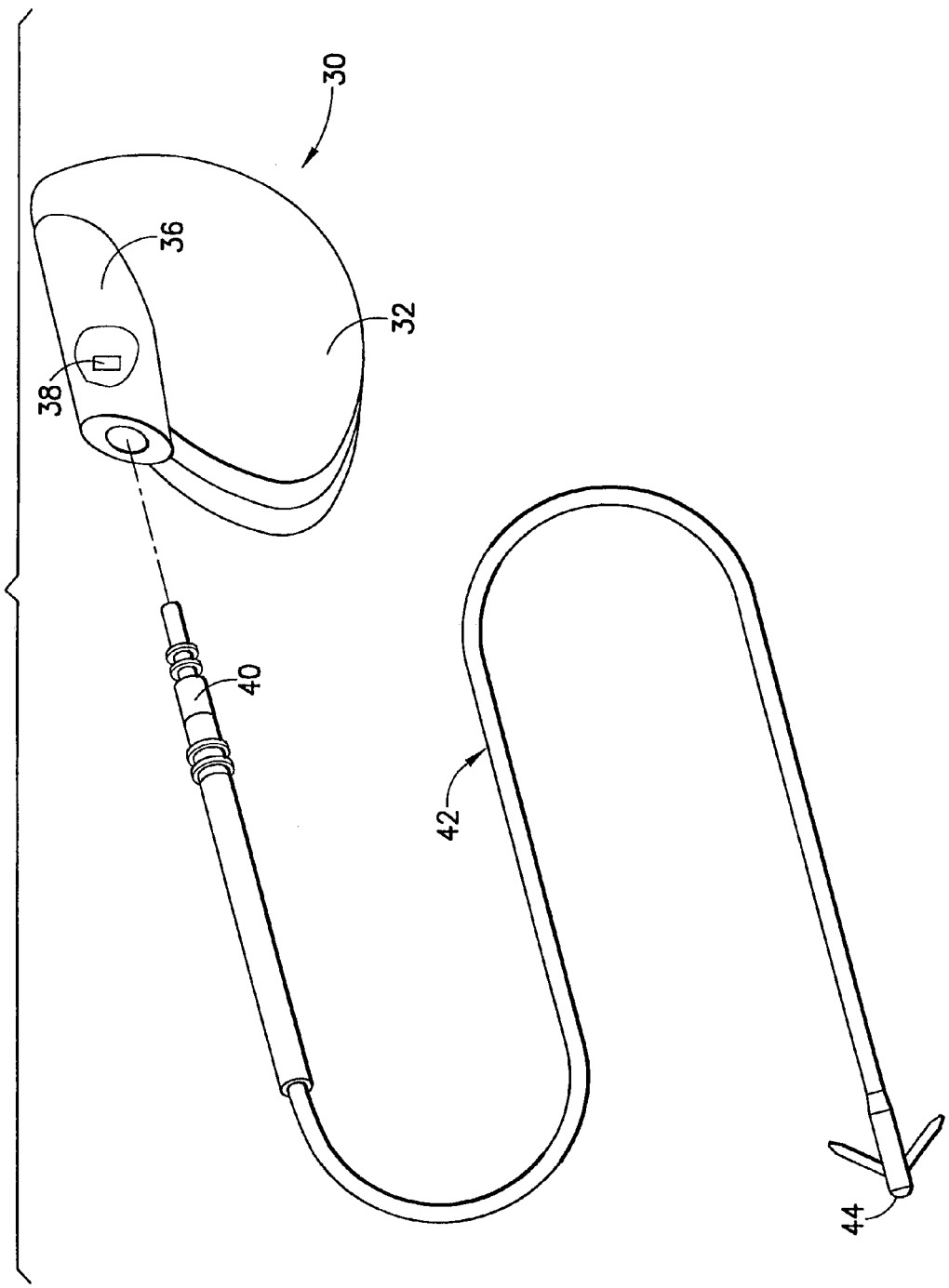
FIG. 2 is a perspective view of an implantable lead embodying the invention in combination with a cardiac stimulation device such as a pacemaker or defibrillator.
Figure 5:
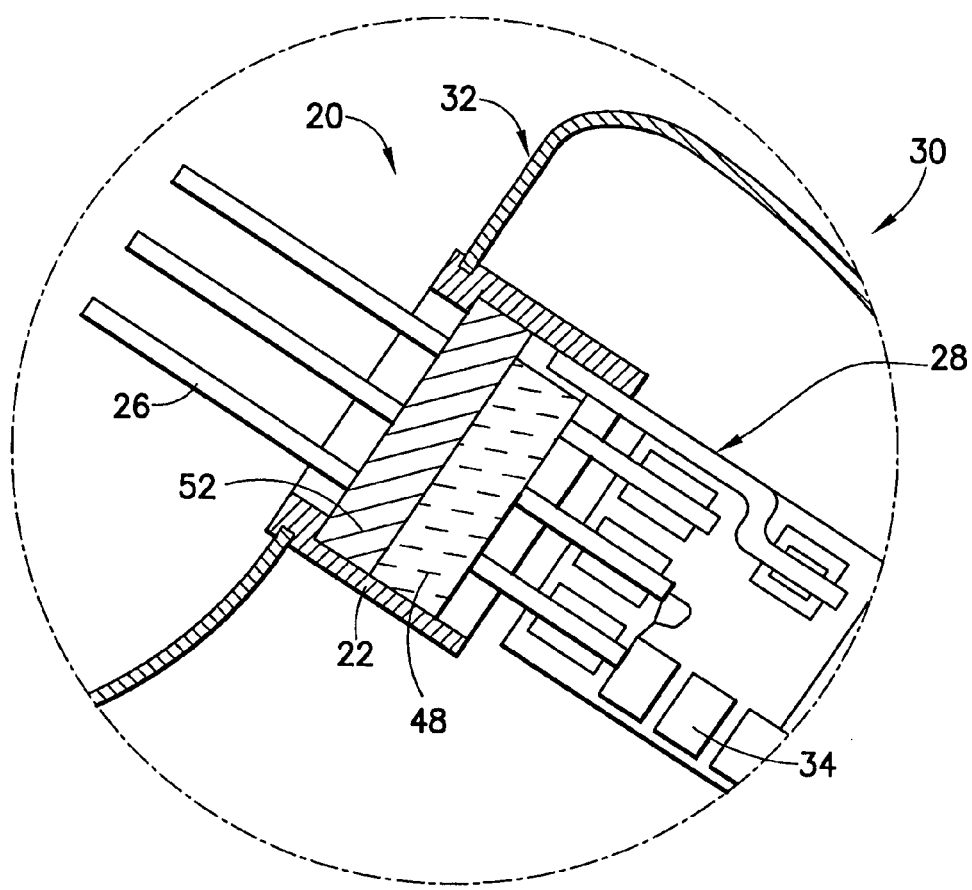
FIG. 5 is a detail side elevation view of a part of the cardiac stimulation device illustrated in FIG. 4.

Referring to FIG. 1, there is shown a perspective view of a feedthrough device 20 incorporating features of the present invention. Although the present invention will be described with reference to the embodiments shown in the drawings, it should be understood that the present invention can be embodied in many alternate forms or embodiments. In addition, any suitable size, shape or type of elements or materials compatible with the invention may be used. The feedthrough device 20 includes a conductive ferrule 22 having an outer peripheral surface 24 defining its outermost boundary. A plurality of lead wires 26 extend through the ferrule 22 but are electrically isolated from the ferrule. A ground wire 28 is coupled to the ferrule and is attached to the feedthrough device within its outermost boundary as defined by the outer peripheral surface 24.

Viewing FIGS. 2–6, the feedthrough device 20 is seen to be a component of a medical implant device 30 for stimulating tissue of a body. The implant device 30 may be, for example, a pacemaker or a defibrillator and, in either event, would include an hermetically sealed housing 32, a battery powered electronic circuit 34 for generating an electrical pulse for delivery to the body tissue, and a connector assembly 36 having at least one contact 38 for engageably receiving a proximal end 40 of a medical electrical lead 42 whose distal end 44 is engageable with the body tissue.

Figure 6:
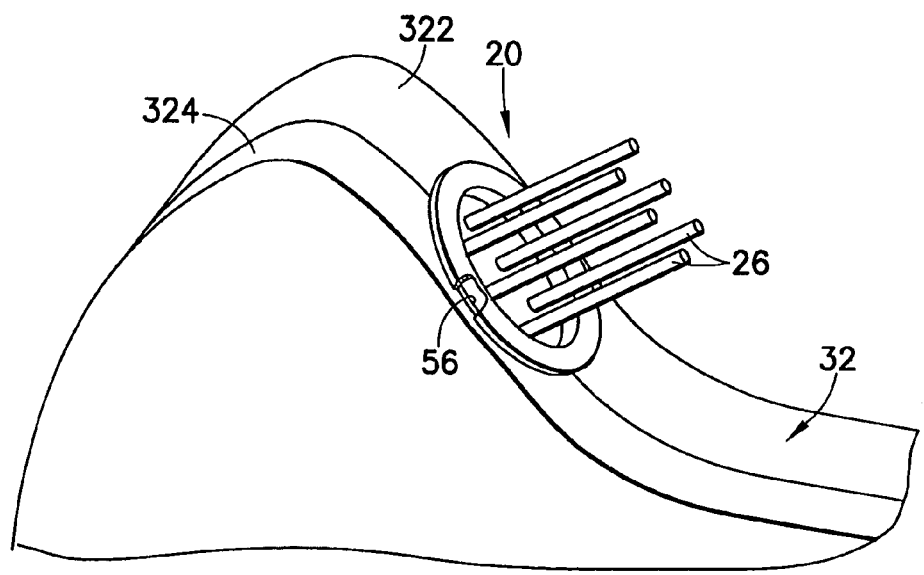
FIG. 6 is a detail perspective view of that portion of the cardiac stimulation device illustrated in FIG. 5.

As most clearly seen in FIG. 6, the feedthrough device 20 is mounted on the housing 32.

Figure 7:
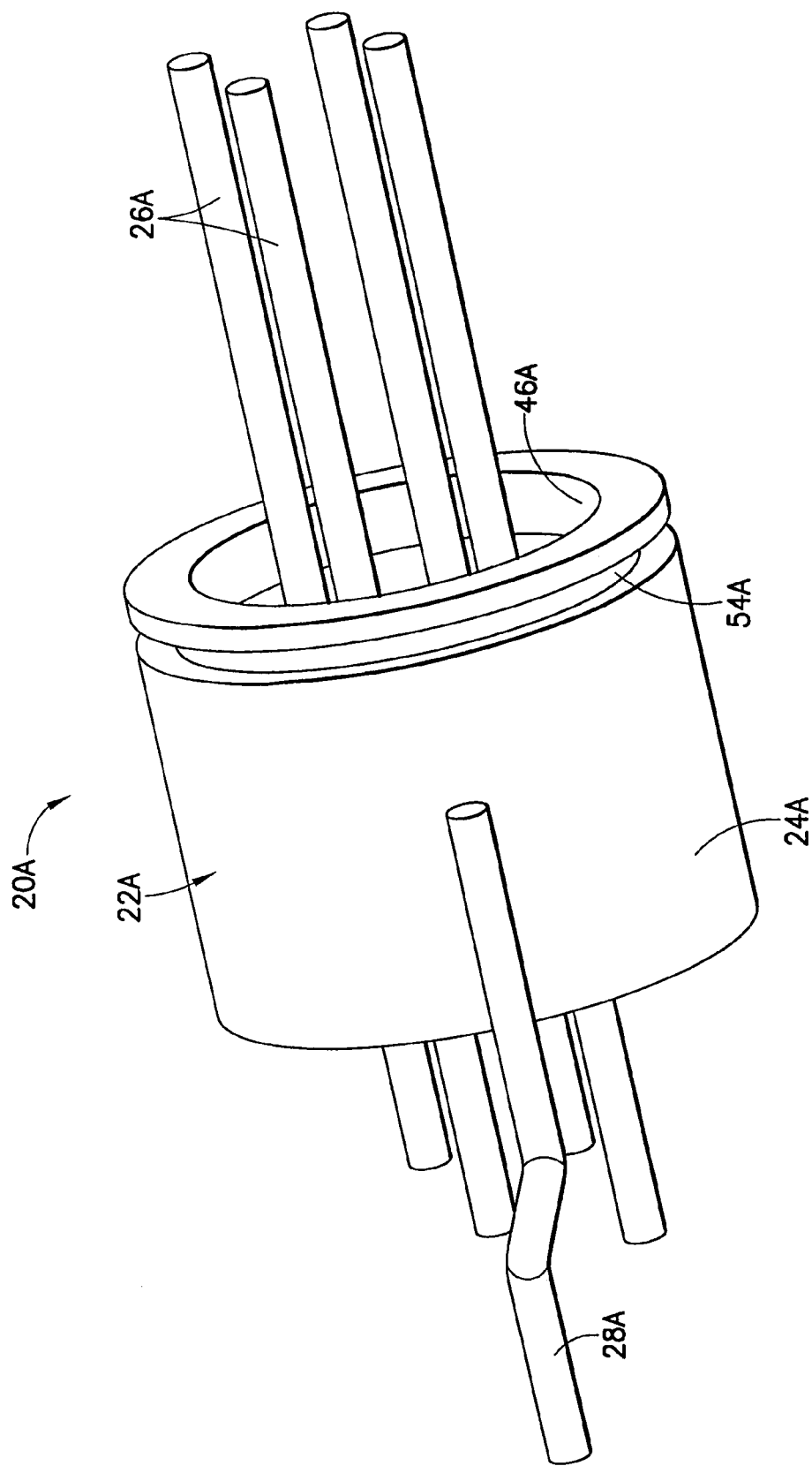
FIG. 7 is a perspective view of a known feedthrough device.
Figure 9:
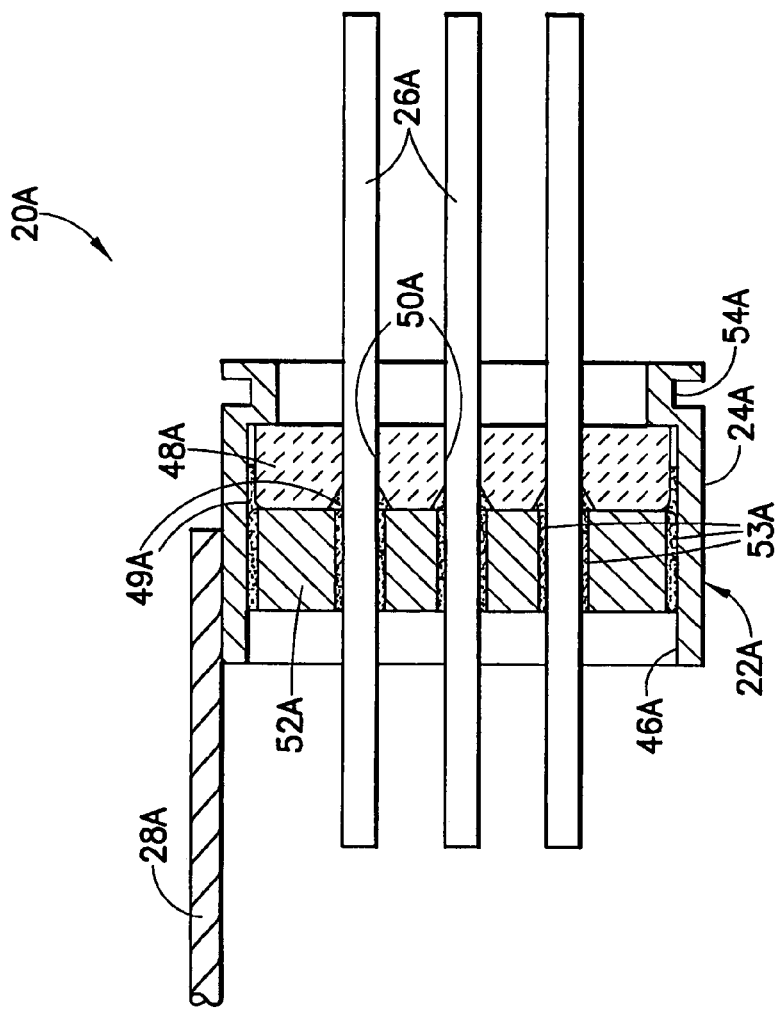
FIG. 9 is a cross section view taken generally along line 9—9 in FIG. 8.
Figure 8:
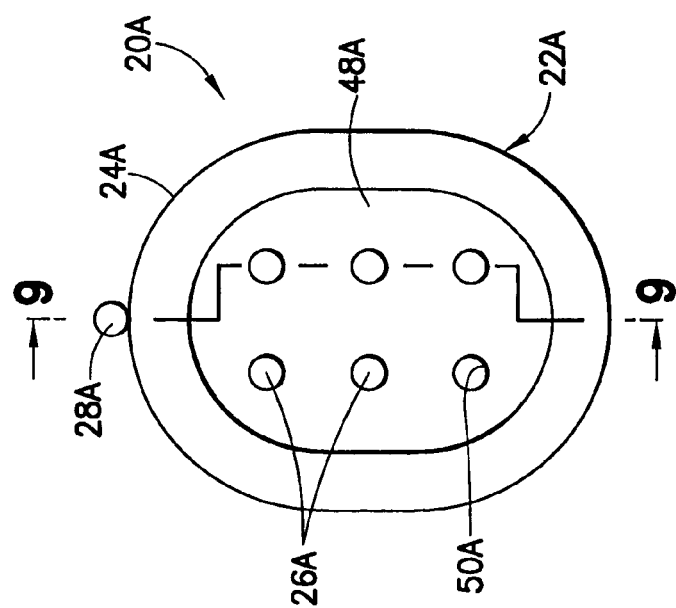
FIG. 8 is an end elevation view of the known feedthrough device illustrated in FIG. 7.

While a more detailed description of the present invention will be related below, before that occurs, it will help to generally describe the prior art which led to the present invention. For this description, turn now initially to FIGS. 7, 8, and 9. Some parts of the explanation may be repetitive of the earlier description with similar numbers employing the suffix "A". As seen, then, in FIGS. 7–9, a known feedthrough device 20A includes a conductive ferrule 22A which may typically be fabricated of titanium, niobium, tantalum, stainless steel, and alloys of those metals and has an outer peripheral surface 24A defining its outermost boundary. The ferrule 22A has an inner peripheral surface 46A defining an opening which extends substantially through its entire length.

Within the opening defined by the surface 46A is a disk-shaped insulator 48A of a ceramic material of which examples may be alumina, zirconia, glass, and combinations of those materials. At least one and preferably a plurality of lead wires 26A extend through associated preformed bores 50A in the insulator and are electrically isolated from the ferrule. The lead wires are composed of an electrically conductive material such as titanium, niobium, tantalum, stainless steel, and alloys of those metals. A disk-shaped filter capacitor 52A is also positioned within the opening in the ferrule defined by the surface 46A adjacent the insulator 48A through which the lead wires 26A extend and is bonded to the inner peripheral surface 46A by the application of suitable conductive epoxy material 53A. The lead wires are in conductive relation with the filter capacitor 52A and are brazed to a metalized surface of the insulator 48A as indicated at 49A. The brazing material may be gold, copper, silver or alloys of those metals. A ground wire 28A which may be composed of platinum or a platinum alloy is seen welded to the outer peripheral surface 24A and thereby electrically coupled to the ferrule 22A but beyond the outer boundary defined by the ferrule. An annular groove 54A is formed at one end of the ferrule 22A for engageably receiving an opening edge 56 (see FIG. 6) in the housing 32. It will be appreciated that the housing 32 is fabricated in two pieces 322, 324 which, when joined and welded to create the hermetically sealed housing 32, encompass and hold fast the ferrule 22A by virtue of the annular groove 54A.

Undesirable aspects of this known construction result from the location of the ground wire 28A which is outside of the outer boundary of the ferrule 22A and the requirement to attach the ground wire to the ferrule by welding which thereby adds a step to the assembly procedure and increases the overall size of the feedthrough.

Figure 11:
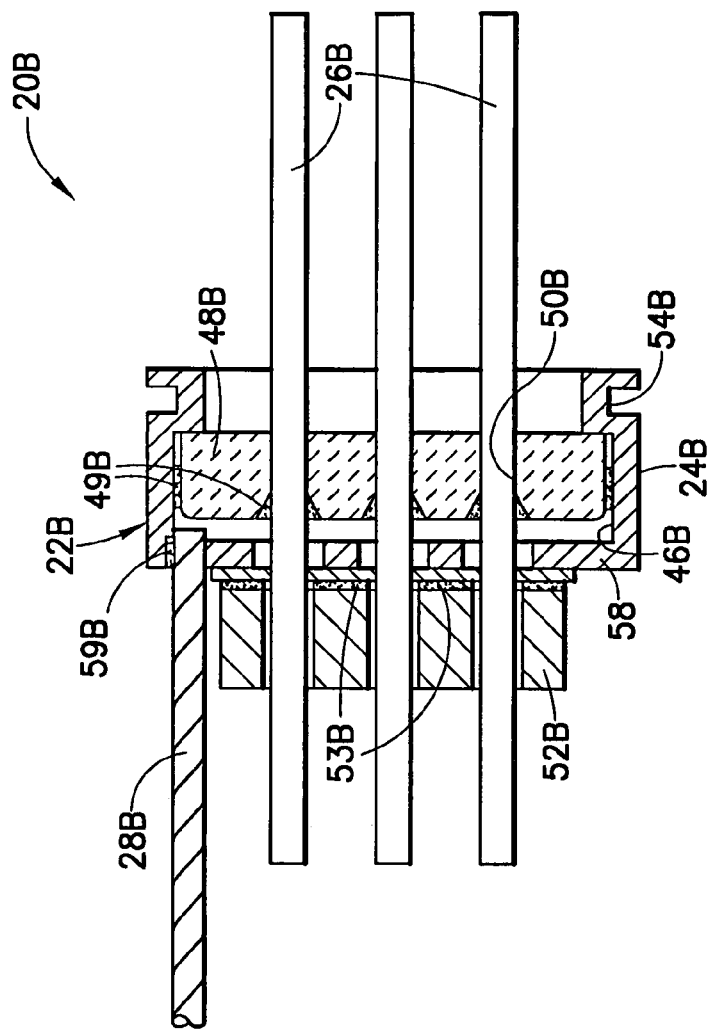
FIG. 11 is a cross section view taken generally along line 11—11 in FIG. 10.
Figure 10:
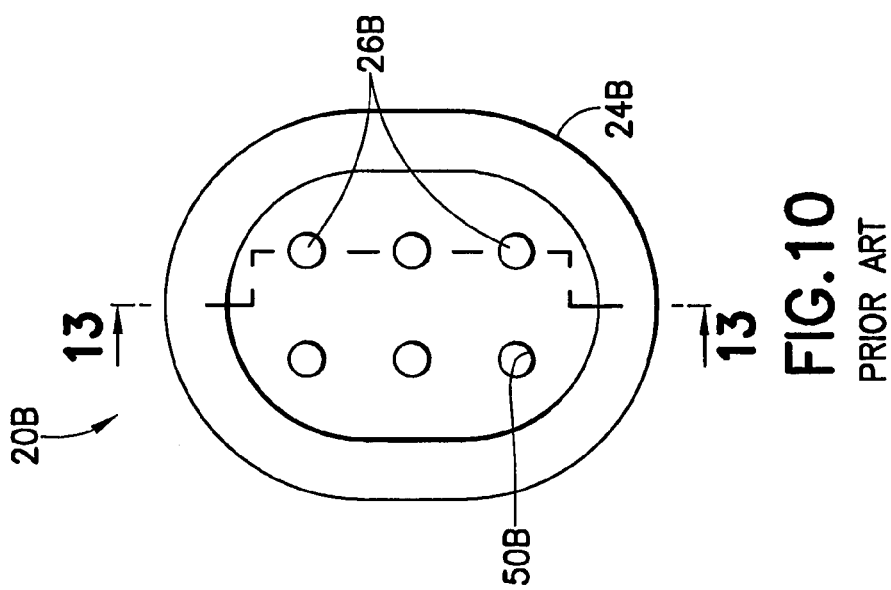
FIG. 10 is an end elevation view of another known feedthrough device.
Figure 17:
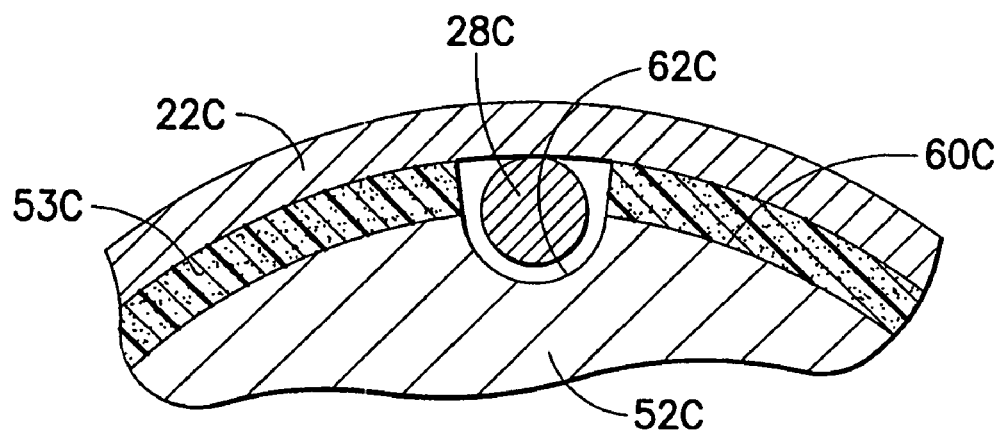
FIG. 17 is a detail cross section view taken generally along line 17—17 in FIG. 16.
Figure 18:
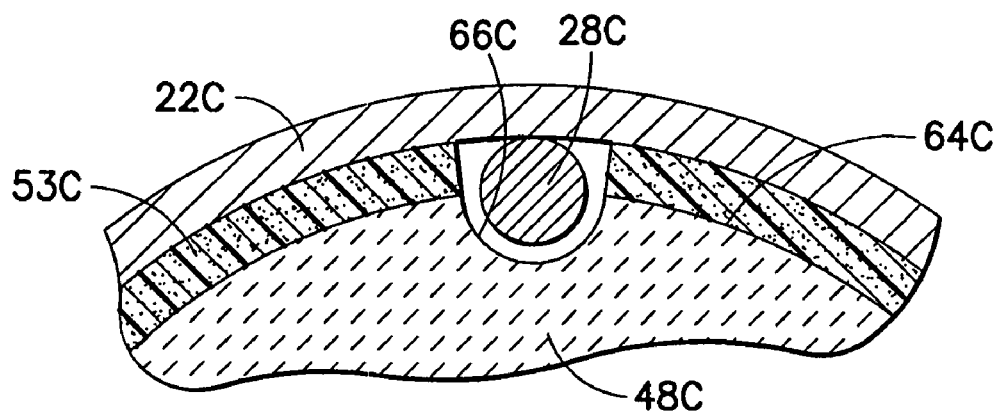
FIG. 18 is a detail cross section view taken generally along line 18—18 in FIG. 16.

Another prior art construction indicated by reference numeral 20B is illustrated in FIGS. 10 and 11 as before, some parts of the explanation may be repetitive of the earlier description although similar numbers using the suffix "B" will be employed.

Within the opening defined by an inner peripheral surface 46B is a disk-shaped insulator 48B of a ceramic material of which examples may be alumina, zirconia, glass, and combinations of those materials. At least one and preferably a plurality of lead wires 26B extend through associated preformed bores 50B in the insulator and are electrically isolated from the ferrule. The lead wires may be of an electrically conductive material such as titanium, niobium, tantalum, stainless steel, and alloys of those metals. In this instance, a disk-shaped filter capacitor 52B is positioned outside of the opening in the ferrule defined by the surface 46B and is bonded to an electrically conductive ground plate 58 by the application of suitable conductive epoxy material 53B. The ground plate 58 is integral with the ferrule 22B and has electrical continuity with the ferrule. Again, the lead wires are in conductive relation with the filter capacitor 52B and are brazed, as at 59B, to a metalized surface of the insulator 48B. The brazing material may be gold, copper, silver or alloys of those metals. A ground wire 28B which may be composed of platinum or a platinum alloy is seen welded, as at 49B, to the inner peripheral surface 46B and thereby electrically coupled to the ferrule 22B. Also, as earlier described, an annular groove 54B is formed at one end of the ferrule 22B for engageably receiving an opening edge 56 in the housing 32. As earlier explained, the housing 32 is fabricated in two pieces 322, 324 which, when joined and welded to create the hermetically sealed housing 32, encompass and hold fast the ferrule 22B by virtue of the annular groove 54B.

We are now returning to the description of the present invention and initially to FIGS. 12 and 13 as well as to FIGS. 1–6. Materials of components employed in the present invention will be the same as those mentioned for the prior art constructions unless stated otherwise. The ferrule 22 has an inner peripheral surface 46 defining an opening which extends substantially through its entire length. Within the opening defined by the surface 46 is a disk-shaped ceramic insulator 48. At least one and preferably a plurality of lead wires 26 extend through associated pre-formed bores 50 in the insulator and are electrically isolated from the ferrule. A disk-shaped filter capacitor 52 is also positioned within the opening in the ferrule 22 defined by the surface 46 adjacent the insulator 48 through which the lead wires 26 extend and is bonded to the inner peripheral surface 46 by the application of suitable conductive epoxy material 53. The lead wires are in conductive relation with the filter capacitor 52 and are brazed, as at 49, to a metalized surface of the insulator 48.

An outer peripheral surface 60 of the filter capacitor 52 has a counterbore 62 to locate and freely receive the end of the ground wire 28 which is coupled by welding, as at 59, to the inner peripheral surface 46 of the ferrule 22. Preferably, conductive epoxy 53 is also applied between the inner peripheral surface 46 of the ferrule 22 and the outer peripheral surface 60 of the filter capacitor 52 to bond the filter capacitor to the ferrule and provide electrical continuity between those components. Conductive epoxy material 53 is also applied between each lead wire 26 and its associated bore through the filter capacitor 52.

As with the prior art constructions described, an annular groove 54 is formed at one end of the ferrule 22 for engageably receiving an opening edge 56 (see FIG. 6) in the housing 32. Since the housing 32 is fabricated in two pieces 322, 324, when they are joined and welded to create the hermetically sealed housing 32, these pieces encompass and hold fast the ferrule 22 by virtue of the annular groove 54.

The construction illustrated in FIGS. 12–14 is particularly desirable because of the availability of the counterbore 62 to locate and freely receive the end of the ground wire such that it is located within the outermost boundary of the ferrule 22.

Turn now to FIGS. 15, 16, 17, and 18 for the description of another embodiment of the invention indicated by reference numeral 20C. In this instance, again, some parts of the description may be repetitive of earlier descriptions and similar numbers using the suffix "C" will here be employed.

The ferrule 22C has an inner peripheral surface 46C defining an opening which extends substantially through its entire length. Within the opening defined by the surface 46C is a disk-shaped ceramic insulator 48C. At least one and preferably a plurality of lead wires 26C extend through associated pre-formed bores 50C in the insulator and are electrically isolated from the ferrule. A disk-shaped filter capacitor 52C is also positioned within the opening in the ferrule 22C defined by the surface 46C adjacent the insulator 48C through which the lead wires 26C extend and is bonded to the inner peripheral surface 46C by the application of suitable conductive epoxy material 53C. The lead wires are in conductive relation with the filter capacitor 52C and are brazed, as at 49C, to a metalized surface of the insulator 48C.

An outer peripheral surface 60C of the filter capacitor 52C has a counterbore 62C to freely receive the end of the ground wire 28C and, in similar fashion, an outer peripheral surface 64C of insulator 48C has a counterbore 66C to freely receive the end of the ground wire 28C. The ground wire 28C is coupled by welding, as at 59C, to the inner peripheral surface 46C of the ferrule 22C. Preferably, conductive epoxy 53C is applied between the inner peripheral surface 46C of the ferrule 22C and the outer peripheral surface 60C of the filter capacitor 52C to bond the filter capacitor to the ferrule and provide electrical continuity between those components. Conductive epoxy material 53C is also applied between each lead wire 26C and its associated bore through the filter capacitor 52C.

This is a preferred construction to that described with the aid of FIGS. 12–14. In this instance, counterbores 62C and 66C are formed in both the filter capacitor 52C and insulator 48C, respectively, to easily locate and receive the free end of the ground lead 28C. Then, with the ground lead so positioned, it is brazed to the insulator and to the ferrule during the same operation for attaching the lead wires 26C to the insulator 48C. This construction eliminates the welding operation which is otherwise necessary to attach the ground lead 28C to the ferrule 22C.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A feedthrough device comprising:
a conductive ferrule having an outer peripheral surface defining the outermost boundary of the feedthrough device;
an insulator;
at least one lead wire electrically isolated from the ferrule supported on and extending through the insulator;
a filter capacitor within the ferrule, adjacent the insulator through which the lead and in conductive relation therewith with the at least one lead wire; and
a ground wire electrically coupled to the ferrule and located within the outermost boundary of the feedthrough device.

2. A feedthrough device as set forth in claim 1
wherein the ferrule has an inner peripheral surface defining an opening therethrough;
wherein each of the insulator and the filter capacitor has an outer peripheral surface proximate the inner peripheral surface of the ferrule, a counterbore formed in the outer peripheral surface of each of the insulator and filter capacitor; and
wherein an end of the ground wire is received in the counterbores and electrically coupled to the ferrule by brazing.

3. A feedthrough device as set forth in claim 2 wherein conductive epoxy is applied between the inner peripheral surface of the ferrule and the outer peripheral surface of the filter capacitor to bond the filter capacitor to the ferrule and provide electrical continuity therebetween.

4. The feedthrough device of claim 2
wherein the insulator has a metallized surface; and
wherein the ground wire is brazed to the metallized surface.

5. The feedthrough device of claim 2 wherein the brazing material is a metal selected from the group consisting of gold, copper, silver, and alloys thereof.

6. The feedthrough device of claim 2
wherein the conductive ferrule is comprised of titanium;
wherein the insulator is comprised of alumina ceramic;
wherein the ground wire is comprised of platinum or a platinum alloy; and
wherein the brazing material is comprised of gold.

7. The feedthrough device of claim 1 wherein the insulator is a ceramic material selected from the group consisting of alumina, zirconia, glass, and combinations thereof.

8. The feedthrough device of claim 1 wherein the conductive ferrule comprises a metal selected from the group consisting of titanium, niobium, tantalum, stainless steel, and alloys thereof.

9. The feedthrough device of claim 1 wherein the lead wire comprises a metal selected from the group consisting of niobium, platinum, platinum/iridium, titanium, tantalum, tungsten, molybdenum and alloys thereof.

10. A feedthrough device as set forth in claim 1
wherein the ferrule has an inner peripheral surface defining an opening therethrough;
wherein each of the insulator and the filter capacitor has an outer peripheral surface proximate the inner peripheral surface of the ferrule; and
wherein an end of the ground wire is coupled by welding to the inner peripheral surface of the ferrule.

11. A feedthrough device as set forth in claim 10 wherein the outer peripheral surface of the filter capacitor has a counterbore therein to freely receive the end of the ground wire.

12. A feedthrough device as set forth in claim 10 wherein conductive epoxy is applied between the inner peripheral surface of the ferrule and the outer peripheral surface of the filter capacitor to bond the filter capacitor to the ferrule and provide electrical continuity therebetween.

13. The feedthrough device of claim 10 wherein the insulator is a ceramic material selected from the group consisting of alumina, zirconia, glass, and combinations thereof.

14. The feedthrough device of claim 10 wherein the conductive ferrule comprises a metal selected from the group consisting of titanium, niobium, tantalum, stainless steel, and alloys thereof.

15. The feedthrough device of claim 10 wherein the lead wire comprises a metal selected from the group consisting of niobium, platinum, platinum/iridium, titanium, tantalum, tungsten, molybdenum and alloys thereof.

16. The feedthrough device of claim 10 wherein the brazing material is a metal selected from the group consisting of gold, copper, silver, and alloys thereof.

17. The feedthrough device of claim 10
wherein the conductive ferrule is comprised of titanium;
wherein the insulator is comprised of alumina ceramic; and
wherein the ground wire is comprised of platinum or a platinum alloy.

18. A feedthrough device as set forth in claim 1 wherein:
the ferrule has an inner peripheral surface defining an opening therethrough;
at least one of the insulator and the filter capacitor has an outer peripheral surface proximate the inner peripheral surface of the ferrule and a counterbore formed in the outer peripheral surface; and
an end of the ground wire is received in the counterbore and electrically coupled to the ferrule.

19. The feedthrough device of claim 18 wherein a counterbore is formed in both of the filter capacitor and the insulator.

20. A medical implant device comprising a feedthrough comprising:
a lead wire;
a conductive ferrule comprising an opening therein of sufficient size and shape to accommodate the lead wire and an insulator;
the insulator disposed in the opening in the conductive ferrule, adapted to accommodate the lead wire and support the lead wire in nonconductive relation to the conductive ferrule; and
a ground wire coupled to the conductive ferrule and coupled to the insulator in a single braze joint.

21. The medical implant device of claim 20
wherein the medical implant device comprises a housing; and
wherein the feedthrough device is coupled to the housing, thereby forming a hermetic seal with the housing while allowing the lead wire to pass into the housing.

22. The medical implant device of claim 20 wherein the medical implant device comprises a cardiac pacemaker.

23. The medical implant device of claim 20 wherein the medical implant device comprises a cardiac defibrillator.

24. A feedthrough device comprising:
a conductive ferrule having an inner peripheral surface;
an insulator;
at least one lead wire electrically isolated from the ferrule supported on and extending through the insulator;
a filter capacitor adjacent the insulator and in conductive relation with the at least one lead wire; and
a ground wire electrically coupled to the ferrule and received in a counterbore located proximate the inner peripheral surface.

25. The feedthrough device of claim 24 wherein the filter capacitor has an outer peripheral surface proximate the inner peripheral surface and the counterbore is in the outer peripheral surface.

26. The feedthrough device of claim 24 wherein each of the filter capacitor and insulator has an outer peripheral surface proximate the inner peripheral surface and the counterbore is in each of the outer peripheral surfaces.

* * * * *